United States Patent
Frankel

(10) Patent No.: US 7,860,605 B2
(45) Date of Patent: *Dec. 28, 2010

(54) SYSTEM FOR CONTROLLING ACCESS TO AND SEGREGATING DISPENSED ITEMS

(75) Inventor: Mark E. Frankel, Lower Gwynedd, PA (US)

(73) Assignee: Quiq, LLC, Plymouth Meeting, PA (US)

( * ) Notice: Subject to any disclaimer, the term of this patent is extended or adjusted under 35 U.S.C. 154(b) by 539 days.

This patent is subject to a terminal disclaimer.

(21) Appl. No.: 11/894,768

(22) Filed: Aug. 21, 2007

(65) Prior Publication Data

US 2008/0103626 A1 May 1, 2008

Related U.S. Application Data

(63) Continuation-in-part of application No. 11/820,564, filed on Jun. 21, 2007, and a continuation-in-part of application No. 11/476,220, filed on Jun. 27, 2006, now Pat. No. 7,483,766.

(51) Int. Cl.
*G06F 17/00* (2006.01)

(52) U.S. Cl. ................ 700/236; 700/242; 700/244; 221/97

(58) Field of Classification Search .......... 700/236, 700/242, 244; 221/97
See application file for complete search history.

(56) References Cited

U.S. PATENT DOCUMENTS

| | | | |
|---|---|---|---|
| 4,767,917 A | 8/1988 | Ushikubo | |
| 4,812,629 A * | 3/1989 | O'Neil et al. | ........... 221/13 |
| 4,847,764 A | 7/1989 | Halvorson | |
| 5,014,875 A | 5/1991 | McLaughlin et al. | |
| 5,431,299 A | 7/1995 | Brewer et al. | |
| 5,797,515 A | 8/1998 | Liff et al. | |
| 5,883,370 A | 3/1999 | Walker et al. | |
| 6,032,155 A | 2/2000 | de la Huerga | |
| 6,067,524 A | 5/2000 | Byerly et al. | |
| 6,109,774 A | 8/2000 | Holmes et al. | |
| 6,219,587 B1 | 4/2001 | Ahlin et al. | |
| 6,330,491 B1 | 12/2001 | Lion | |
| 6,352,200 B1 | 3/2002 | Schoonen et al. | |
| 6,529,801 B1 | 3/2003 | Rosenblum | |
| 6,564,121 B1 | 5/2003 | Wallace et al. | |
| 6,636,780 B1 | 10/2003 | Haitin et al. | |

(Continued)

*Primary Examiner*—Timothy R Waggoner
(74) *Attorney, Agent, or Firm*—Howard IP Law Group, PC

(57) ABSTRACT

In one embodiment, a system for controlling access to and segregating dispensable items comprises a vending machine that contains the dispensable items to be vended. The vending machine includes an access control mechanism responsive to selection of one of the dispensable items for causing the vending machine to activate and vend the selected item. Transaction information associated with each of the vended items is stored in memory. The vending machine further includes a port on an exterior of the machine and adapted to receive items previously vended from the vending machine for return. A repository is located on the interior of the machine and operably connected to the port for quarantining the returned items, whereby the returned items are separated from the items to be vended. A sensor may be provided for sensing the returned items and causing the system to update transaction information to indicate that the sensed item has been returned to the machine.

18 Claims, 8 Drawing Sheets

U.S. PATENT DOCUMENTS

| | | |
|---|---|---|
| 6,766,218 B2 | 7/2004 | Rosenblum |
| 6,769,228 B1 | 8/2004 | Mahar |
| 6,834,755 B2 * | 12/2004 | Jay ........................ 198/418.6 |
| 6,892,941 B2 | 5/2005 | Rosenblum |
| 6,985,870 B2 | 1/2006 | Martucci et al. |
| 7,123,989 B2 | 10/2006 | Pinney et al. |
| 7,194,333 B2 | 3/2007 | Shoenfeld |
| 7,474,938 B2 * | 1/2009 | Poliner ........................ 700/242 |
| 2002/0062175 A1 | 5/2002 | Lion |
| 2003/0050731 A1 | 3/2003 | Rosenblum |
| 2003/0074218 A1 | 4/2003 | Liff et al. |
| 2004/0215369 A1 | 10/2004 | Rosenblum |
| 2005/0049746 A1 | 3/2005 | Rosenblum |
| 2005/0075908 A1 | 4/2005 | Stevens |
| 2005/0281601 A1 | 12/2005 | Papetti |

* cited by examiner

SYSTEM FOR CONTROLLING ACCESS TO AND SEGREGATING DISPENSED ITEMS

RELATED APPLICATIONS

This application is a continuation-in-part of and claims priority of U.S. patent application Ser. No. 11/476,220 filed Jun. 27, 2006 now U.S. Pat. No. 7,483,766 and U.S. patent application Ser. No. 11/820,564 filed Jun. 21, 2007, the entire disclosures of which are hereby incorporated by reference as if being set forth in their entireties herein.

FIELD OF THE INVENTION

In general, the present invention relates to systems and methods that are used to control access to and convey pharmaceuticals in an automated manner and that safeguards against prescription fraud, preparation error and control and segregation of undistributed items.

BACKGROUND

When a person is sick, they commonly use the services of a professional healthcare provider. In the standard course of operation, healthcare providers regularly examine and diagnose patients in their offices. Typically, a sick patient will meet with the healthcare provider in his/her office. The healthcare provider will diagnose the illness and suggest a course of action to treat the illness. Often, the suggested course of action involves the taking of a medication. If the selected medication is a controlled pharmaceutical, the healthcare provider writes a prescription for the patient. The patient takes the prescription to a pharmacy, wherein a pharmacist fills the prescription. As such, sick patients must proceed through a two-step process before they receive medication for their ailment. The patient must first visit with a healthcare provider to obtain a prescription. The patient must then visit with a pharmacist to have the prescription filled.

The two-step process of obtaining medication for an ailment presents many problems for a patient. The obvious problem is one of inconvenience. It takes time to visit both a physician's office and a pharmacy. It also takes time for a pharmacy to fill a prescription. Consequently, there can be a delay of many hours between when a physician hands a patient a prescription for a medication and the time that the patient has that medication in hand.

Furthermore, just because a patient is given a prescription does not mean that the patient will fill the prescription. A patient may believe that the physician is wrong in their diagnosis. Alternatively, a patient may procrastinate, hoping the aliment will pass without medication. A patient may also lose the prescription, forget about the prescription or purposely not fill the prescription for a variety of financial, religious and/or personal reasons.

The other problems associated with the two-step process of receiving medications are much less obvious, but no less important. When a patient arrives at a pharmacy, the patient must hand the pharmacist the prescription. The pharmacist must assume that the prescription is proper for both the patient and the illness being treated. In other words, the pharmacist must assume that the doctor did not make any error in writing the prescription and has handed the correct prescription to the correct patient. The pharmacist must then decipher the physician's handwriting and understand what has been prescribed in what amounts. If the pharmacist misreads the prescription in any way, the prescription will be incorrectly prepared.

Assuming the physician did not err in issuing the prescription and the pharmacist did not err in reading the prescription, the pharmacist must then properly fill the prescription and label the prescription. If the pharmacist errs in either filling or labeling the prescription, the patient may take the wrong medication or may take the right medication, but the wrong dosage. The patient may also be given the proper medication, in the proper dosage, but with incorrect dosing instructions.

Finally, once a prescription is prepared and labeled, it must be given to the correct patient. Most pharmacies do not ask to see identification from patients. The prescription is often just handed to the first person who asks for the prescription and pays for the prescription.

Most patients assume that the prescription given to them at the pharmacy is correct. If a patient is handed the wrong prescription, there is a good chance that the patient will take that medication without ever reading the label on the bottle.

In addition to all the problems that may accidentally occur in traditional systems, many people also attempt fraud to acquire pharmaceutical prescriptions. Such people take advantage of the many problems of the system to forge, falsify, and steal pharmaceuticals.

It will therefore be understood that in order for a person to properly receive a prescription, there must be no human error in writing, handling, filling, labeling and delivering the prescription. Although the system works correctly the vast majority of the time, human error will always be present. Thousands of such errors occur every year. These errors could result, either directly or indirectly, in deaths, permanent injury, illness, harmful drug interactions and untreated disease. This creates liabilities to pharmacists and doctors resulting in increased healthcare costs for everyone.

Despite training and safety protocols, the only way to reduce human error is to minimize the points in the system where human error can occur. To prevent physicians from writing illegible prescriptions, many electronic prescription systems have been created that electronically transmit prescriptions to pharmacies. Such prior art systems are exemplified by U.S. Pat. No. 6,067,524 to Byerly, entitled Method And System For Automatically Generating Advisory Information For Pharmacy Patients Along With Normally Transmitted Data; and U.S. Pat. No. 5,883,370 to Walker, entitled Automated Method For Filling Drug Prescriptions.

A common place where errors occur is in the filling, labeling and delivery of the prescription by the pharmacist. One way to minimize human error in these processes is to create automated machines that convey prepackaged pharmaceuticals.

There are many ways to convey prepackaged goods to the public using automation. A common way to convey prepackaged goods is through the use of vending machines. Vending machines can vend any product that is placed into the vending machines, including prepackaged pharmaceuticals. Vending machines can also be left accessible to the public at all times, thereby enabling a person to fill a prescription at their own convenience. Vending machines specifically configured to vend prescription pharmaceuticals are exemplified by U.S. Pat. No. 5,797,515, to Liff, entitled Method For Controlling A Drug Dispensing System.

Replacing a human pharmacist with an automated vending machine presents its own set of problems. First, the vending machine must be manually filled with the proper medications. Human error may cause the vending machine to be incorrectly filled. Furthermore, as most everyone has experienced, vending machines do not always vend properly. Merchandise gets jammed. Sometimes nothing vends from the machine, sometimes two products accidentally vend from the machine.

A need therefore exists for an improved prescription preparation and conveying system that eliminates as much human error as possible by using automating processes. A need also exists for an improved automated conveying system for prescription pharmaceuticals that safeguards against many errors that are prevalent in prior art automated systems.

SUMMARY

In one embodiment, a system for controlling access to and segregating dispensable items comprises a vending machine that contains the dispensable items to be vended. The vending machine includes an access control mechanism responsive to selection of one of the dispensable items for causing the vending machine to activate and vend the selected item. Transaction information associated with each of the vended items is stored in memory. The vending machine further includes a port on an exterior of the machine and adapted to receive items previously vended from the vending machine for return. A repository is located on the interior of the machine and operably connected to the port for quarantining the returned items, whereby the returned items are separated from the items to be vended. A sensor may be provided for sensing the returned items and causing the system to update transaction information to indicate that the sensed item has been returned to the machine.

In one embodiment, the present invention is a system and method of prescribing and conveying regulated pharmaceuticals. A stock of prepackaged units of use is provided. A prepackaged unit-of-use may be a sealed bottle, jar, vial or package that contains a prescribed course of medication, for example. The stock of prepackaged units of use are kept in a vending machine. The activation of the vending machine is controlled by a central processing unit. The system also contains a data reading unit that may be located in or near the vending machine.

Upon the completion of a patient's diagnosis, a physician may prescribe a regulated pharmaceutical. If the pharmaceutical is present within the vending machine, the physician enters the prescription into a terminal. The prescription is read by a processor such as the central processing unit that controls the vending machine. The central processing unit identifies the location of the pharmaceutical in the vending machine and awaits a proper vending code.

In an exemplary embodiment of the present invention, the physician hands the patient an electronic key card. The key card is encoded with the vending code needed to activate the vending machine. The patient carries the key card to the vending machine. The key card is read by the data reading unit. If the code on the key card matches the prescription code previously entered by a physician, the vending machine vends the prepackaged unit-of-use.

Through the use of sensors and label codes, the system verifies that the prepackaged unit-of-use has correctly vended from the machine and that the prepackaged unit-of-use is correct.

BRIEF DESCRIPTION OF THE DRAWINGS

For a better understanding of the present invention, reference is made to the following description of an exemplary embodiment thereof, considered in conjunction with the accompanying drawings, in which.

DETAILED DESCRIPTION

Before embarking on a detailed discussion the following should be understood. The present invention system and method can be used to convey and control access to dispensable items or materials other than pharmaceuticals. For example, it is contemplated that various regulatable substances may be dispensed including but not limited to expensive items, hazardous materials, or other substances that require control or regulation. For example, the method and system of the present invention can be utilized in a factory setting where industrial tools such as expensive work tools, bits or dies are controlled in their delivery to the factory floor. However, the present invention is particularly well suited for use in the prescribing, conveying and controlling of prescription pharmaceuticals. Accordingly, the present invention apparatus, system and method is described for use in conveying prescription pharmaceuticals in order to set forth the best mode contemplated for the invention.

Figure 1:
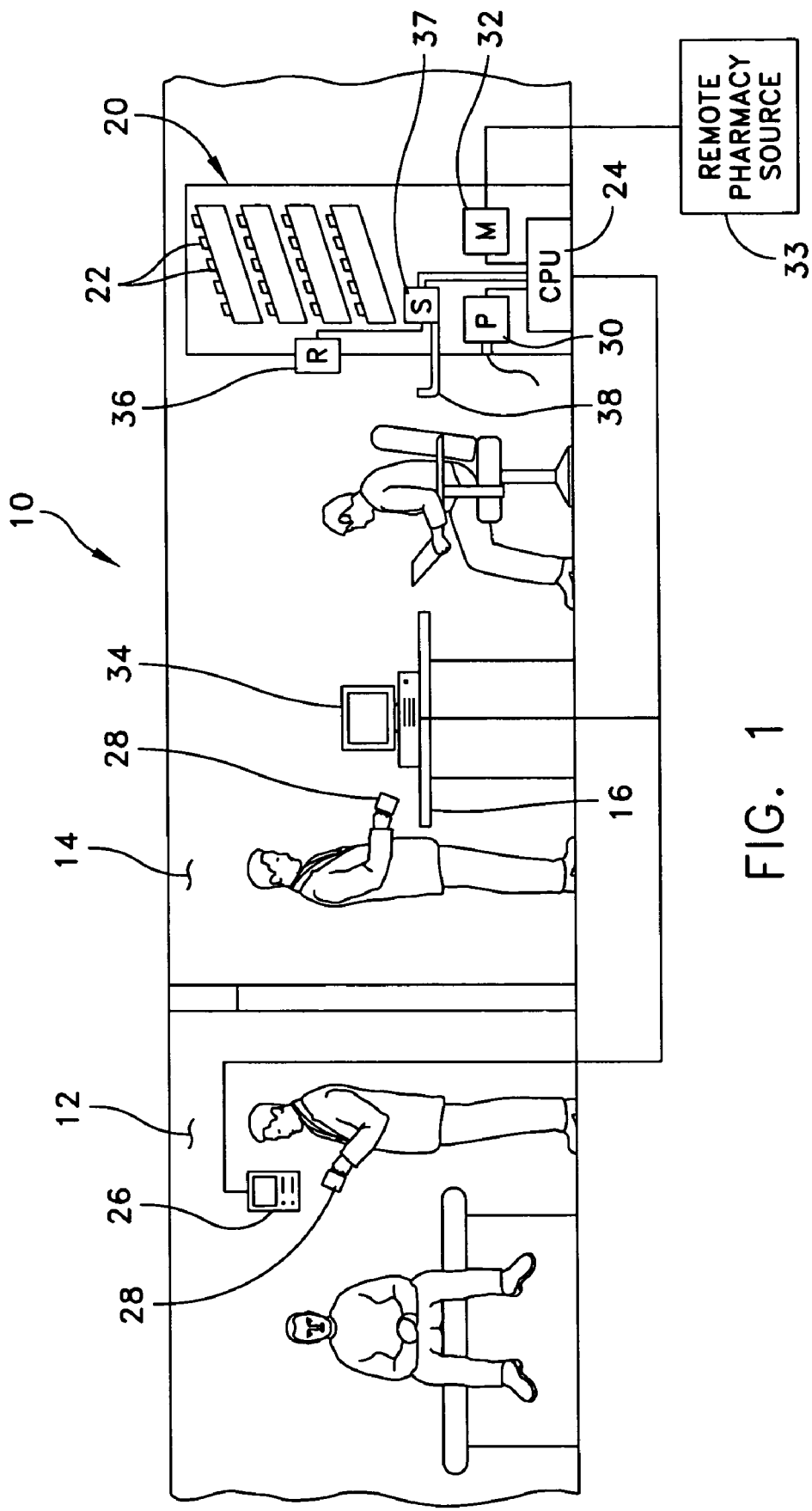
FIG. 1 is an exemplary schematic representation of a physician's office containing the present invention system.

Referring to FIG. 1, a schematic of a physician's office 10 is shown that contains an exemplary embodiment of the present invention system. The physician's office 10 includes an examination room 12 and an office area 14. The examination room 12 is the room where physicians physically examine patients. The office area 14 typically is a restricted area that is only used by office personnel. The office area 14 usually has a countertop 16 that separates the office area 14 from public areas used by the coming and going patients.

The present invention system utilizes a prescription fulfillment or prescription vending machine 20 to store prepackaged items or units of use. A unit-of-use may be a bottle, jar, vial, tube, syringe, package or other receptacle that is prefilled with pharmaceutical. In one embodiment, the unit of use is prefilled in a volume large enough to complete a course of treatment. The vending machine 20 is preferably kept in the restricted office area 14. However, the vending machine 20 may be present in public areas for direct access by patients.

The vending machine 20 contains a stock of prepackaged units of use 22. The prepackaged units of use 22 kept in the vending machine 20 depend upon the type of physician's office. In a pediatric physician's office, the vending machine 20 might, among other things, contain various antibiotics in dosages suitable for children of different weights and ages. In a geriatric physician's office, the vending machine might contain, among other things, prepackaged units of use for arthritis and hypertension. It will therefore be understood that the vending machine 20 will be stocked with the prepackaged units of use 22 that are most typically prescribed by the physicians in that office.

The vending machine 20 contains a central processing unit 24. The central processing unit 24 controls the vending mechanisms of the vending machine 20. The central processing unit 24 also keeps track of the stock inventory carried and conveyed by the vending machine 20.

A data input terminal 26 is provided. Although the data input terminal 26 can be located anywhere, it is preferred that each of the examination rooms 12 be provided with a data input terminal 26. The data input terminal 26 can be a panel that is mounted to a wall, a tabletop computer terminal or a portable handheld device. Each of the data input terminals 26 is coupled to the central processing unit 24 using either a hard wire or wireless (e.g. radio frequency) network.

In one configuration, each of the data input terminals 26 can only be activated by an authorized individual (e.g. authorized physician) from that office. The data input terminal 26 may be activated by the physical input of an access code or password. The data input terminal 26 may also be activated by swiping an identification card or providing some biometric data, such as a fingerprint. However, in the exemplary embodiment, the data input terminal 26 is activated by a radio frequency identification (RFID) tag that is carried by the physician. In this manner, the electronic input interface will automatically activate as the physician approaches that device.

The data input terminal 26 contains a screen. Once activated, the physician can enter a prescription for a pharmaceutical. The number of prepackaged units of use 22 held within the vending machine 20 are limited by the capacity of the vending machine 20. Thus, in an exemplary embodiment, the vending machine 20 is filled with a selection chosen by the health care professionals of that office that are best suited for the patients served by that practice. The selections offered by the vending machine 20 can be presented to the physician on the data input terminal 26 in the form of a selection menu. The physician therefore needs only select one of the menu choices to complete a prescription. However, the data input terminal 26 also enables a physician to custom enter a prescription for any pharmaceutical, even if that pharmaceutical is not carried by the vending machine 20. If a particular pharmaceutical is not contained in the vending machine 20, a printed prescription will print for the patient to take to a pharmacy in the traditional manner.

Key card sets may also be provided. Each of the key card sets contains two key cards 28 that are electronically matched. The key cards 28 are preferably kept secure prior to use. The key cards 28 are therefore held by the physician or are kept in a secure manner near the data input terminal 26 in the examination room 12. Each of the key cards 28 in each key card set contains a vending code. In a preferred embodiment, the vending code is contained in an RFID tag that is present on each of the key cards 28. The data input terminal 26 can therefore passively read the vending code from the key card 28 just by holding the key card 28 proximate the data input terminal 26 when prompted by the data input terminal.

It will be understood that although an RFID tag is preferred, the vending code can be read in other manners. For instance, the key card 28 may contain a magnetic strip, barcode, digital data storage chip, magnetic storage disk, optical storage disk or other readable data sequence that can read to the data input terminal 26. Alternatively, the key card 28 may just contain a printed vending code that can be manually entered into the data input terminal 26.

Regardless to the method of data transfer, what is of importance is that the vending code is read by the data input terminal 26. That vending code becomes associated with the prescription data that was just entered into the data input terminal.

Once prescription data and a corresponding vending code are entered into the data input terminal 26, both the prescription data and the vending code are automatically forwarded to the central processing unit 24 in the vending machine 20.

The central processing unit 24 in the vending machine 20 is coupled to a printer 30. The printer 30 can be a tabletop printer. However, in the shown embodiment, the printer 30 is contained within the structure of the vending machine 20.

A modem 32 is coupled to the central processing unit 24. The modem 32 enables the central processing unit 24 to communicate with a remote pharmacy source 33, via some existing telecommunications network. In this manner, the central processing unit 24 can keep the remote pharmacy source 33 aware of the inventory and age of the prepackaged units of use 22 within the vending machine 20. Periodically, or as needed, the remote pharmacy source 33 will send a person to restock, replace or remove the prepackaged units of use 22 from the vending machine 20.

The central processing unit 24 also communicates with the physician's electronic medical record system, for example, via an office computer 34. In this manner, when a prescription is written for a particular patient, that information may be saved to the medical records of that patient.

Figure 2:
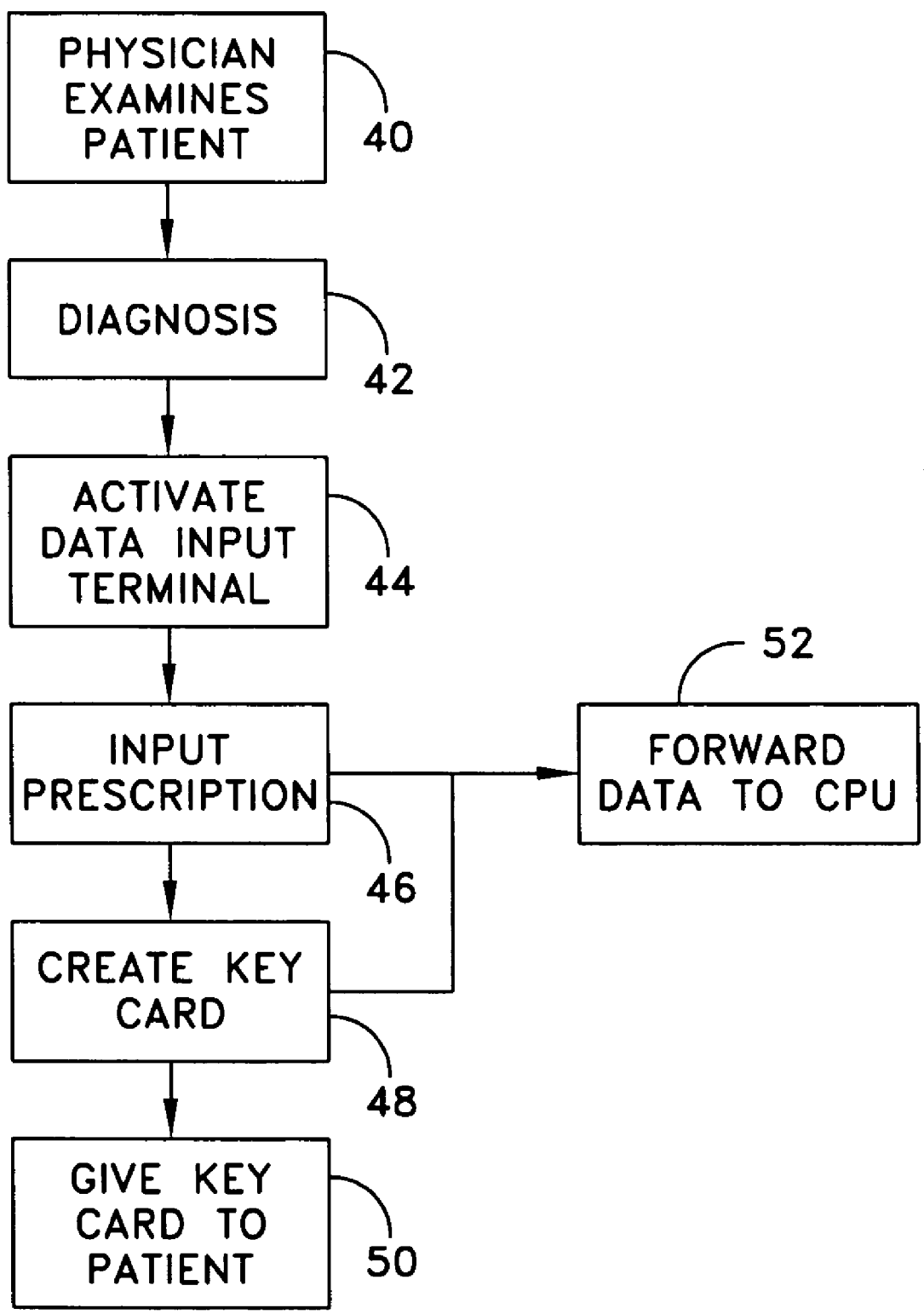
FIG. 2 is a block diagram showing another part of the methodology used by the present invention system.

Having described an exemplary physical layout of the present invention system, the system's method of operation can now be described. Referring to FIG. 1 in conjunction with FIG. 2, it can be seen that the present invention system may be contained within a physician's office 10 or other healthcare facility, such as a hospital. A patient is taken to an examination room 12, wherein the patient is examined by a physician. See Block 40. The physician diagnoses the cause of illness in the patient and conceives of a treatment. See Block 42. If the treatment includes the need for a prescription, the physician activates the data input terminal 26. See Block 44. Using the data input terminal 26, the physician enters a prescription. See Block 46. The physician also takes a key card set. The physician reads the vending code from one key card 28 into the data input interface so that the vending code becomes associated with the prescription data. See Block 48. The second key card 28 is handed to the patient for later use at the vending machine 20. See Block 50.

The prescription information and vending code that were entered into the data input terminal 26 are forwarded to the central processing unit 24. See Block 52.

Figure 3:
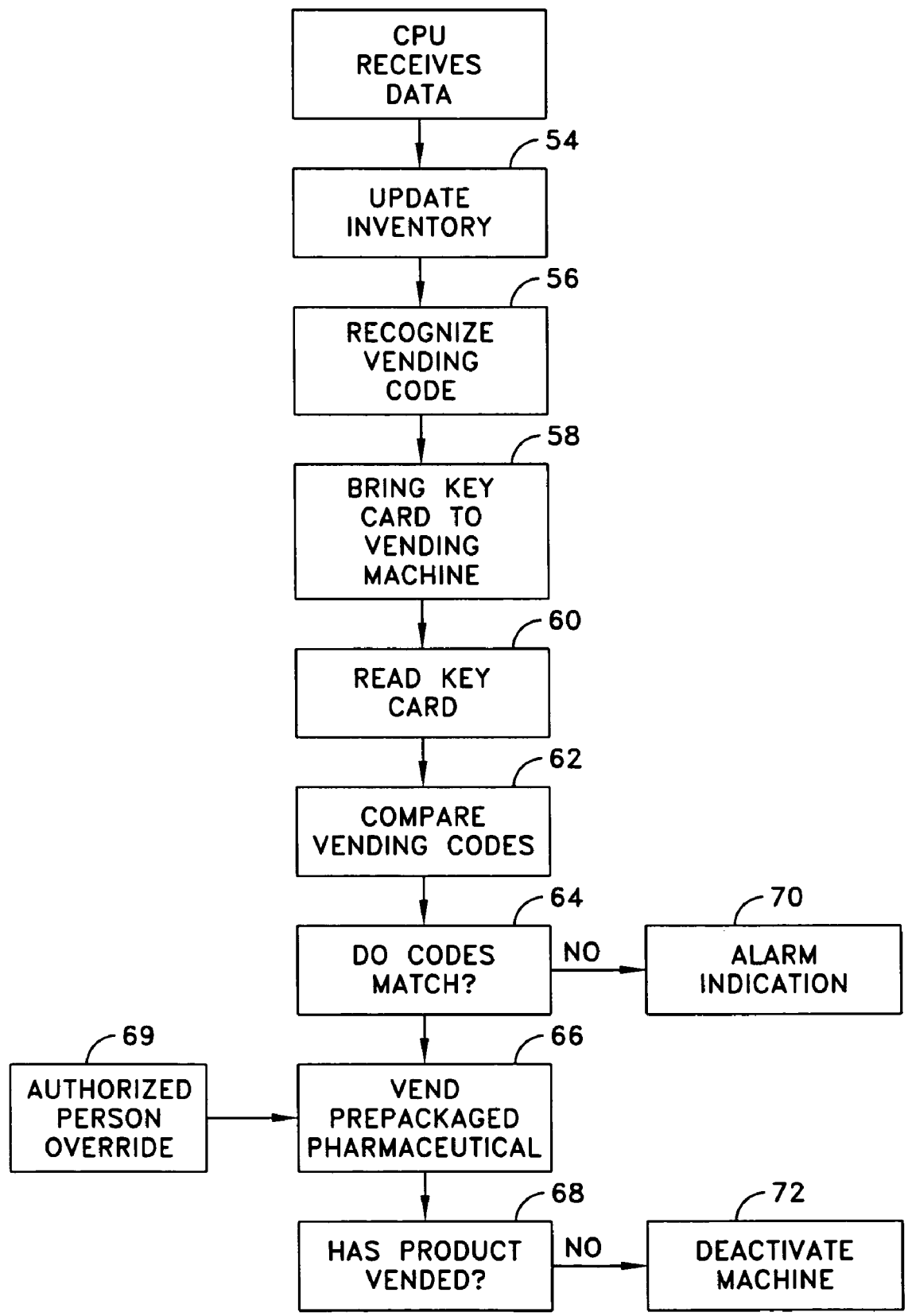
FIG. 3 is a block diagram showing yet another part of the methodology used by the present invention system.

Referring to FIG. 3 in conjunction with FIG. 1, it will be understood that once the central processing unit 24 receives prescription data from the data input terminal 26, it deducts the prescription from the inventory of the vending machine 20, even though the vending machine 20 has not yielded the prescription. The central processing unit 24 immediately updates inventory information, as is indicated by Block 54. In this manner, if another physician in another office were to prescribe that same medication, the physician would know if that medication were available within the vending machine 20 for dispensing.

In the illustrated embodiment, the vending machine 20 contains a data reading unit 36. Such a location is exemplary, and it will be understood that the data reading unit can be remote from vending machine 20 provided it remains in communication with the vending machine 20. The data reading unit 36 can read the key card 28 of the patient. The type of data reading unit 36 depends upon the type of key card 28 being used. For example, if the key card 28 is a card with a magnetic strip, the data reading unit 36 is a card swipe reader. In the preferred embodiment, the key card 28 contains an RFID tag. As such, the data reading unit 26 would be an RFID reader. Regardless, what is of importance is that the data reading unit 36 is capable of reading data from the key card 28.

A patient brings the key card 28 to the vending machine 20 or hands it to an office worker who brings it to the vending machine 20. See Block 58. The key card 28 is then read by the data reading unit 36. See Block 60. Once the key card 28 is read, the central processing unit 24 matches the vending code from the key card 28 to the vending code that was previously received with the prescription data from the data input terminal 26. See Block 62. If the vending codes match, the central processing unit 24 then enables the vending machine 20 and vends the appropriate prepackaged unit-of-use 22. See Blocks 64 and 66.

It will therefore be understood that the vending machine 20 does not have selection buttons in the manner of a traditional vending machine. Rather, the vending machine 20 automatically vends only after the key card 28 is read by the vending machine 20 and compared to a vending code. The data in the vending code controls which of the prepackaged pharmaceuticals will be vended when the vending machine 20 is activated. The chance of an incorrect selection being made by human error is therefore eliminated.

The need for the proper key card can be circumvented by an authorized person. Using a master key card, or the key card that was kept by the physician, a physician or a member of the physician's staff can cause the vending machine 20 to vend. See Block 69. Alternatively, a physician can over-ride the requirement of a key card when the physician enters a prescription into the system. In this manner, a prepackaged unit-of-use 22 can be retrieved in a more direct fashion for a patient from the vending machine 22. This may be helpful in various circumstances, including but not limited to a patient who is, for example homebound or otherwise unable to come to the office.

Since the vending machine 20 is automatically activated by the vending code (e.g. on a key card 28) there is no concern about a person pressing the wrong selection buttons on vending machine 20 and/or receiving the wrong medication. Accordingly, the only way a patient can receive the incorrect prescription is if the vending machine 20 is filled incorrectly or fails to vend properly.

A sensor 37 can be placed in the receiving tray 38 of the vending machine 20. The sensor 37 is coupled to the central processing unit 24. As is indicated by Block 68, the sensor 37 detects whether or not a prepackaged pharmaceutical 22 has been conveyed into the receiving tray 38 after the vending machine 20 has vended. If no prepackaged unit-of-use 22 is detected, it can be assumed that the prepackaged unit-of-use 22 got stuck in the vending machine 22 or the vending machine 22 was not filled properly and vended a blank space. If the central processing unit 24 detects any such vending error, the central processing unit 24 can alert the office staff and alert the operator of the vending machine. See Block 70. The vending machine 20 may also automatically deactivate to ensure that a subsequent patient does not receive the prepackaged unit-of-use that may be only temporarily stuck within the vending machine. See Block 72.

The printer 30 is connected to the central processing unit 24. The printer 30 can be located within the vending machine 20 or at some position close to the vending machine 20. Every time the vending machine 20 is activated by the central processing unit 24, the central processing unit 24 sends a print job to the printer. The print job corresponds to the pharmaceutical being conveyed. The print job, once printed, provides information about the pharmaceutical, such as its instructions for use and possible side effects. The printing also contains identification information that helps ensure that the pharmaceutical that was vended was the pharmaceutical that was intended.

Figure 4:
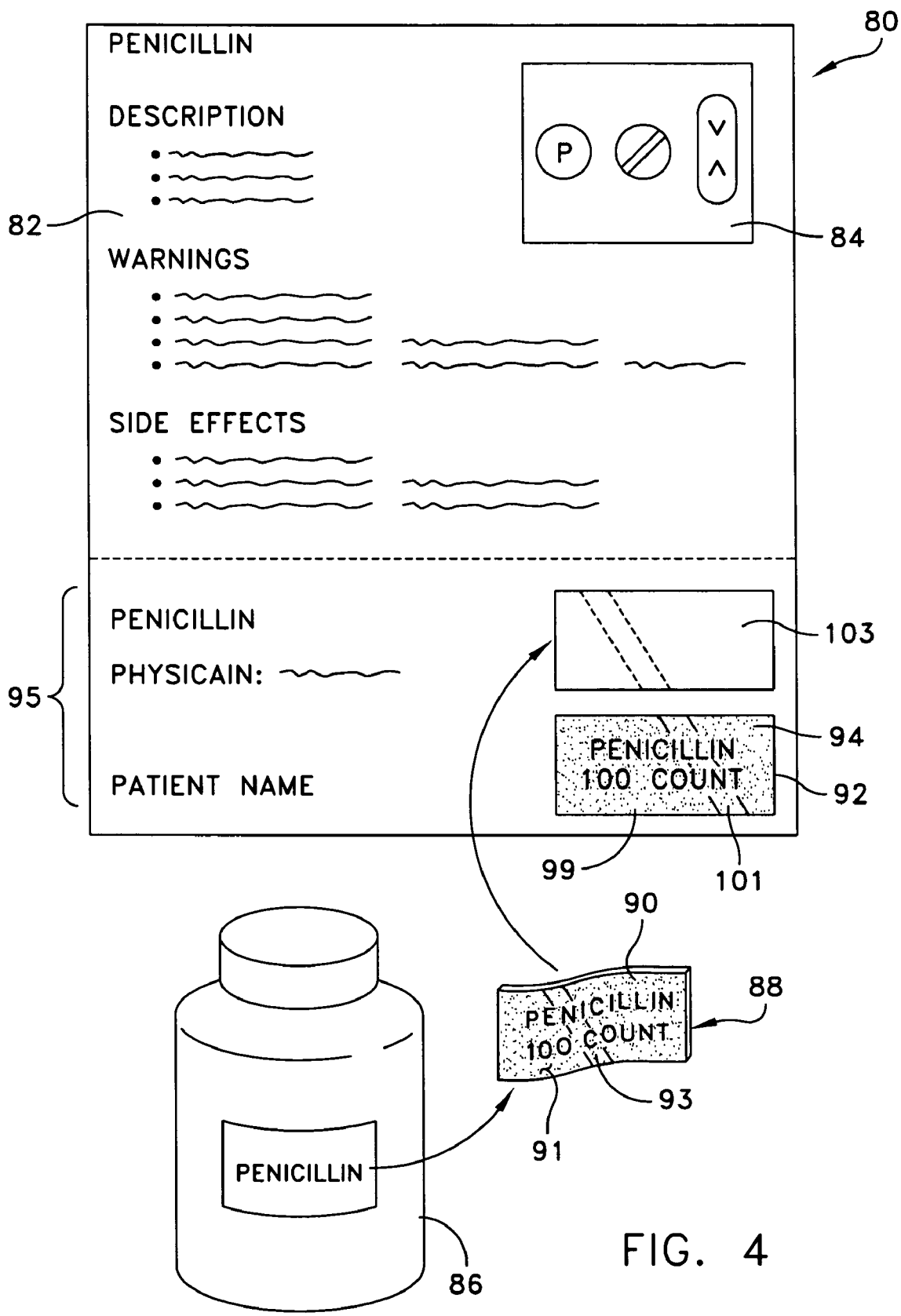
FIG. 4 shows an exemplary printout created by the present invention system and shown with a prepackaged pharmaceutical container.

Referring to FIG. 4, an exemplary embodiment of a printout 80 is shown. The printout 80 has an information section 82 that preferably contains some warnings and/or technical information about the pharmaceutical being conveyed. In one embodiment, the printout 80 also has a picture section 84 that shows color pictures of the pharmaceutical being conveyed. More than one picture may be provided if the pharmaceutical is manufactured by more than one company and comes in different sizes, shapes and/or colors.

A prepackaged pharmaceutical container 86 is also shown in FIG. 4. When such a prepackaged pharmaceutical container 86 vends from the vending machine, it contains a removable label 88. The removable label 88 identifies the pharmaceutical being in the prepackaged container 86 and also provides a code pattern 90 that is unique to that type of prepackaged unit-of-use. The code pattern 90 can be a color code, a numerical code, graphic code or any other visual code. In the exemplary embodiment, the code pattern consists of a color field 91 and an alignment strip 93.

The printout contains a tear-away section 95. A label image 92 is printed onto the tear-away section 95. The label image 92 contains a code pattern 94 that corresponds to the code pattern 90 on the removable label 88 from the prepackaged container 86. The label image 92 also contains a color field 99 and an alignment strip 101.

A label target 103 is printed either immediately above or below the label image 92. The label target 103 shows a person where to place the removable label 88 from the prepackaged container 86.

The removable label 88 is peeled off of the prepackaged container 86 and is applied over the label target 103. Once in this position, the color field 91 of the removable label 88 should be the same color as the color field 99 of the label image 92. Furthermore, the alignment strip 93 of the removable label 88 should align with the alignment strip 101 on the label image 92.

By comparing the removable label 88 to the label 92, two goals are achieved. First, by checking if the code patterns 90, 94 match, it can be seen that the proper prepackaged pharmaceutical container 86 was vended from the vending machine 20. This safeguards against any human error that may have occurred during the filling of the vending machine 20. Second, the tear-away section 95 of the printout is removed and kept by the office staff, thereby providing a permanent record of what was vended from the vending machine 20.

The vending machine 20 is not an ordinary vending machine in the sense that it does not vend for money and it is not a self-contained system. Rather, the vending machine 20 is used as the conveying mechanism for a larger system that is integrated throughout the physician's office.

Figure 5:
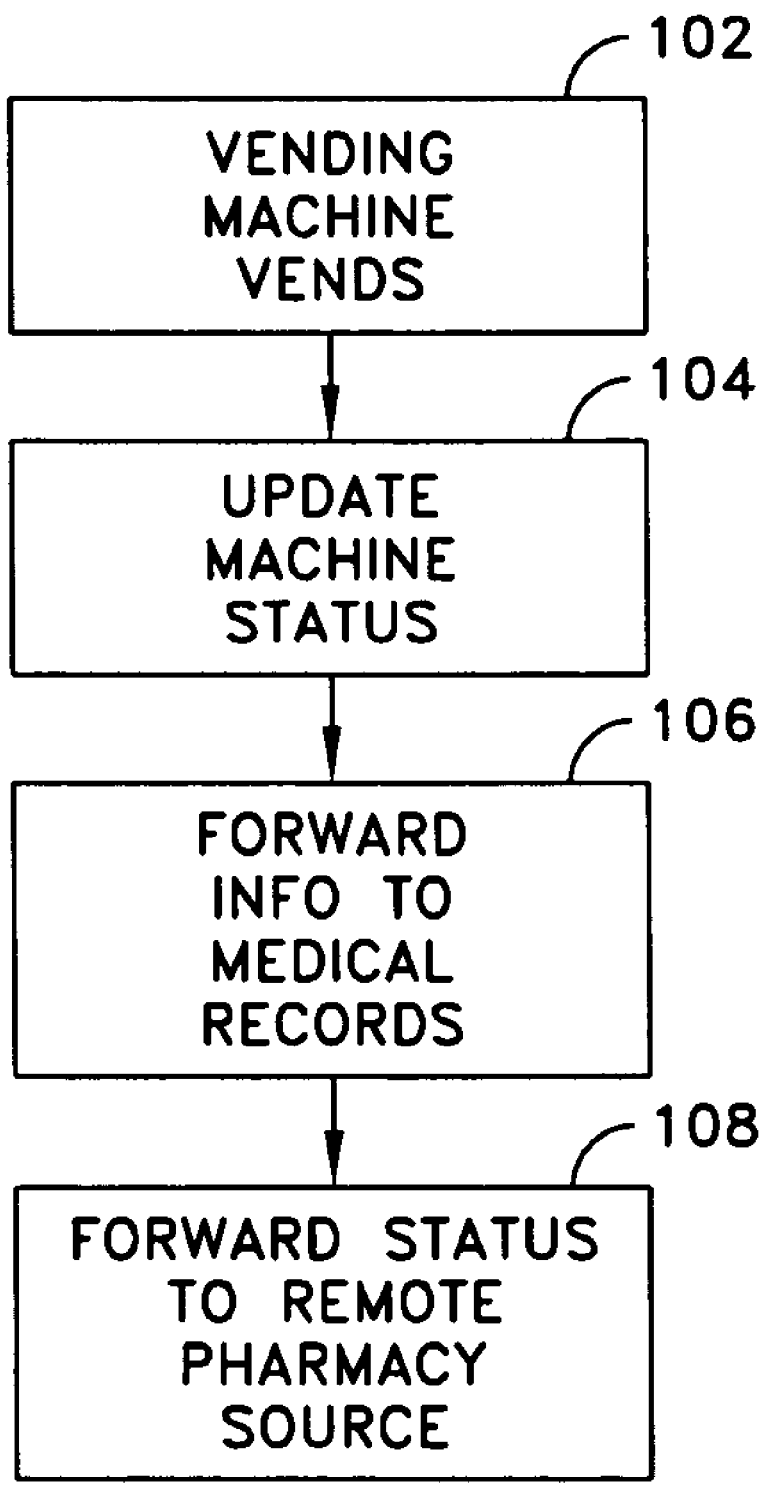
FIG. 5 is a block diagram showing yet another part of the methodology used by the present invention system.

Referring to FIG. 5 in conjunction with FIG. 1, it will be understood that as the vending machine 20 vends, the central processing unit 24 updates the status of the vending machine 20. See Blocks 102 and 104. Information about what was vended and for whom is communicated to the medical record software being run by the computer network in the physician's office. See Block 106. In this manner, a patient's records are automatically updated with the prescription ordered by the physician and the medication that was conveyed.

The central processing unit 24 also forwards update information to the remote pharmacy source 33 who is responsible for filling and maintaining the vending machine 20. See Block 108. In this manner, the remote pharmacy source 33 can periodically come to fill the vending machine 20 before the vending machine 20 ever runs out of a particular type of pharmaceutical.

Figure 6A:
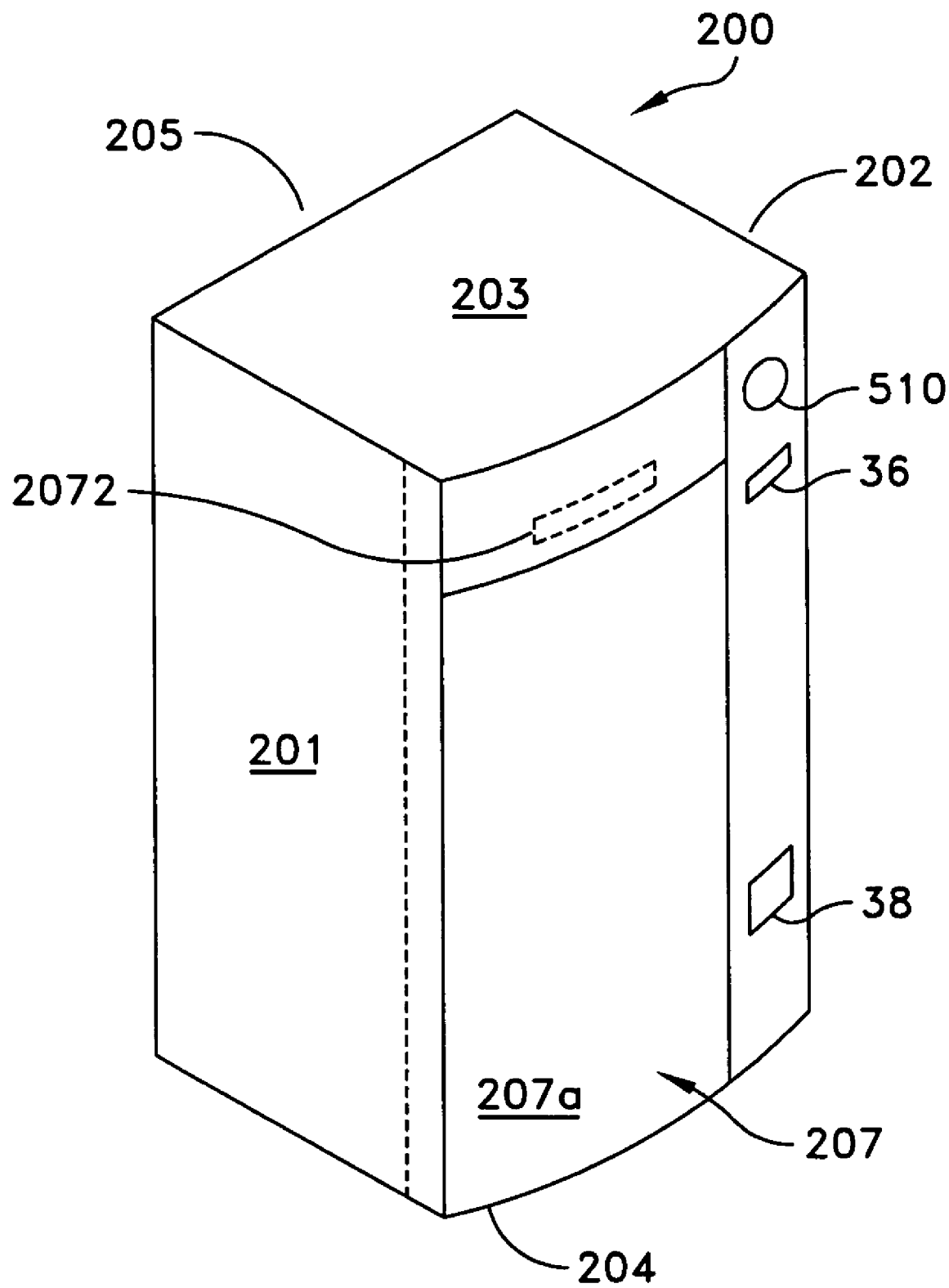
FIGS. 6a and 6b are schematic representations showing major components of a vending machine useful for implementing aspects of the present invention according to an exemplary embodiment.

Referring now to FIG. 6a, there is shown an exemplary embodiment 200 of a vending machine useful for carrying out aspects of the present invention. Like reference numerals have been used to indicate like parts. As shown in the schematic front view of FIG. 6a, vending machine 200 operates as a prescription fulfillment machine for dispensing prepackaged units of use, and further operates to control and quarantine dispensed prepackaged units of use in a secure manner in the event that a dispensed unit cannot be delivered to an authorized recipient. Vending machine 200 includes a hinged exterior door 207 having a first outer portion 207a and a second inner portion 207b (FIG. 6b) opposite the first outer portion. Two sidewalls 201 and 202, a top wall 203, a bottom wall 204 and a back wall 205 together with the exterior door form an enclosure or cabinet space. Exterior door 207 is hingedly coupled to side wall 201. Vending machine 200 further includes an interior insulating door 206 (see FIG. 6b). The exterior door 207 has a security lock system with multiple different locking points in the sidewall. When closed, the exterior door 207 forms an airtight enclosure within the machine 200. The exterior door comprises a solid panel with the exception of an opening or port 510, output dispensing or retrieving tray 38, and optional slot 2072 and reader 36 disposed on the outer surface of door 207. Vending machine 200 includes a port 510 disposed on the exterior door 207 according to an aspect of the present invention. Port 510 is adapted to be sufficiently large to allow depositing of all prepackaged inventory units of use 22 (see FIG. 1) that are dispensed from the vending machine 200 (e.g. via tray 38) to be received into port 510, but not so large as to allow an individual unauthorized physical access to the interior of the cabinet via the port 510. In this manner, the contents deposited into port 510 can be reached only by opening the exterior door 207. Although the port 510 is shown as circular, it is not limited to that shape.

Figure 6B:
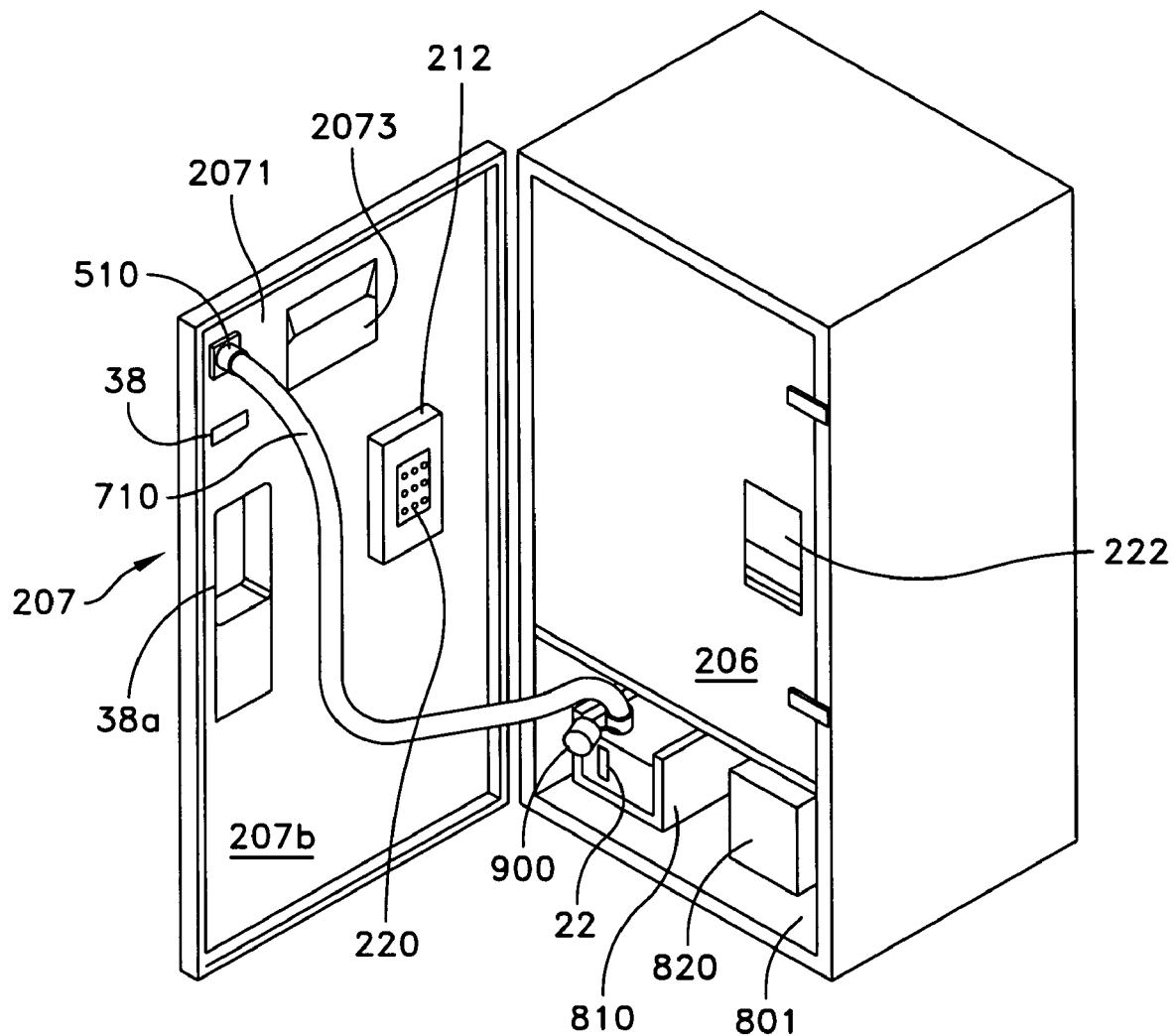

Referring now to FIG. 6b in conjunction with FIG. 6a, a conduit 710 such as a flexible tube or other conveying system has a first end connected to the port 510 on the inner portion 207b of door 207 and is adapted to carry or convey an inventory unit 22 inserted into port 510 from outside the machine, to a quarantine receptacle 810 on the interior of the vending machine 200. In this manner, the item returned to the vending machine cannot be removed except by an individual with authorized access to the interior of the vending machine cabinet 200. In an exemplary embodiment, an insulating door or interior door 206 is positioned between the exterior door 207 and houses the inventory units to be dispensed (not shown) in FIG. 6b. A portion 38a of product retrieval tray may be mounted on the inside of the exterior door 207 wherein a product is retrieved from the cabinet and is passed through the interior insulating door 206 via a product exit door 222 into the product retrieval tray 38a that opens to the exterior 207a of door 207. The retrieved product can be picked from outside the exterior door 207 from the product retrieval tray 38.

An electronic control unit 212 is mounted on the inside of the exterior door 207. The control unit 212 generally controls the functionalities of the vending machine 200. A keypad 220 is installed on the inside of the exterior door 207. The keypad can be used to enter commands for the electronic control unit 212. Below the floor of the interior door 206 lies a compartment area 801 segregated from both the dispensable items behind interior door 206 that contains quarantine receptacle 810. In this manner, the quarantine receptacle 810 may be separately secured to provide enhanced protection and security from unauthorized access while providing clear segregation of mis-vended items.

Referring again to FIGS. 6a and 6b, in an exemplary embodiment, the port 510 is located in the upper portion 2071 of the exterior door 207 and the quarantine receptacle 810 is located in the lower portion 801 of the interior of the vending machine. The conduit may be a flexible tube arranged to convey (e.g. via gravity, pressure, etc.) the inventory unit from port 510 to receptacle 810 by way of example only. In this manner, the returned item is segregated from the other inventory items contained in the vending machine 200 and can be accessed only by opening door 207 (and optional compartment 801 interior door).

A server 820 having a central processing unit is positioned below the cabinet within the compartment area. A server may be any computing device capable of storing and executing a stored set of instructions for controlling the operation of the machine 200. The server 820 is connected to the electronic control unit 212. A power supply is also installed which is connected to the server. The machine 200 may further include a surge protector/power strip to protect the electronic components in the machine 200. A wireless router may be installed below the cabinet within compartment 801. A wireless router is capable of receiving information from a remote unit as well as transmitting information from the server 820.

In a further exemplary embodiment, vending machine 200 may optionally include a slot 2072 formed in exterior door 207 and a corresponding tray 2073 connected to the inner portion of the door 207 communicating with slot 2072. When a "mis-vend" has occurred, a paper form may be filled out that lists the specific inventory item returned, and additional relevant information such as the date and the transaction details. The paper sheet may then be deposited into the slot 2072 adapted for capture in tray 2073 within the interior of the machine 200. As discussed above, the inventory item is returned to and quarantined in the machine via depositing the inventory item 22 in port 510 for capture in receptacle 810 within the interior of the machine. In another embodiment, it is contemplated that the paper sheet may also be deposited via port 510, thereby eliminating the need for slot 2072 and tray 2073.

In another embodiment, the patient information sheet that is printed at the time of delivery is used. As previously described with reference to FIG. 4, the information sheet includes a perforated section that is removable at the bottom of the sheet. The sheet contains all of the personal information pertaining to this transaction. This section is removed and discarded to protect patient security. The top section includes only the general information on the item that was intended to be delivered to the patient. It also has printed on it an alpha numeric code which is specific to the transaction. This section of the patient information sheet may be deposited in the secure receptacle (e.g. port 510 or slot 2072) in the vending cabinet.

In yet another embodiment of the present invention, each of the unit of use packages that constitute the inventory contained within the controlled access cabinet have RFID tags attached thereto. As previously discussed, the tags operate to identify the pedigree and essential information about each specific unit of use package. In the event that a unit of use package needs to be returned to the quarantine area of the cabinet, an RFID reader 900 (see FIG. 6b), located within the interior of the cabinet designed for quarantining such items, identifies the transaction. The RFID reader may be located at various places, such as at or near the entrance of port 510 in the front of the machine, along the conduit 710 or at the receptacle 810. Such positioning may be based on a variety of factors, including but not limited to the configuration of the cabinet, in order to prevent cross talk between other RFID readers within the cabinet (such as reader 38).

In one implementation, vending machine 200 may be adapted or modified from a commercial vending machine such as Jofemar Multiplus unit to include the capabilities and functionalities described herein. Such modifications may include, for example, removal of all internal display units from the upper section of the machine and the addition of a solid panel (e.g. 17 inch by 28 inch panel to the interior of the front upper section; and forming a slot (e.g. about 3 inch by 6 inch aperture) in the upper section of the front panel to allow misvends to be deposited to the quarantine receptacle. Other openings, except for the product dispensing output, are covered on the front panel of the display. The cash dispensing unit is removed from the machine and associated opening along with the key pad and coin slot on the front of the machine. A small port on the rear surface of the machine may be formed to allow cabling to exit the machine.

In the interior of the machine, a server is mounted and configured in the lower or bottom section of the cabinet with appropriate cable connectivity including connection to the control panel to enable appropriate communications and interfacing with the computer and memory storage devices, cable/server connections, and appropriate connectivity with one or more power supplies (e.g. UPS power supply), surge protector/power strips, and mounting of a USB hub and one or more wireless routers. As discussed herein, a conduit and repository is added to the machine to enable misvended items to be quarantined.

Installation of one or more RFID readers and appropriate software/hardware/firmware is implemented within the machine for enabling reading, communicating, storing, and updating information associated with the vended items.

Figure 7:
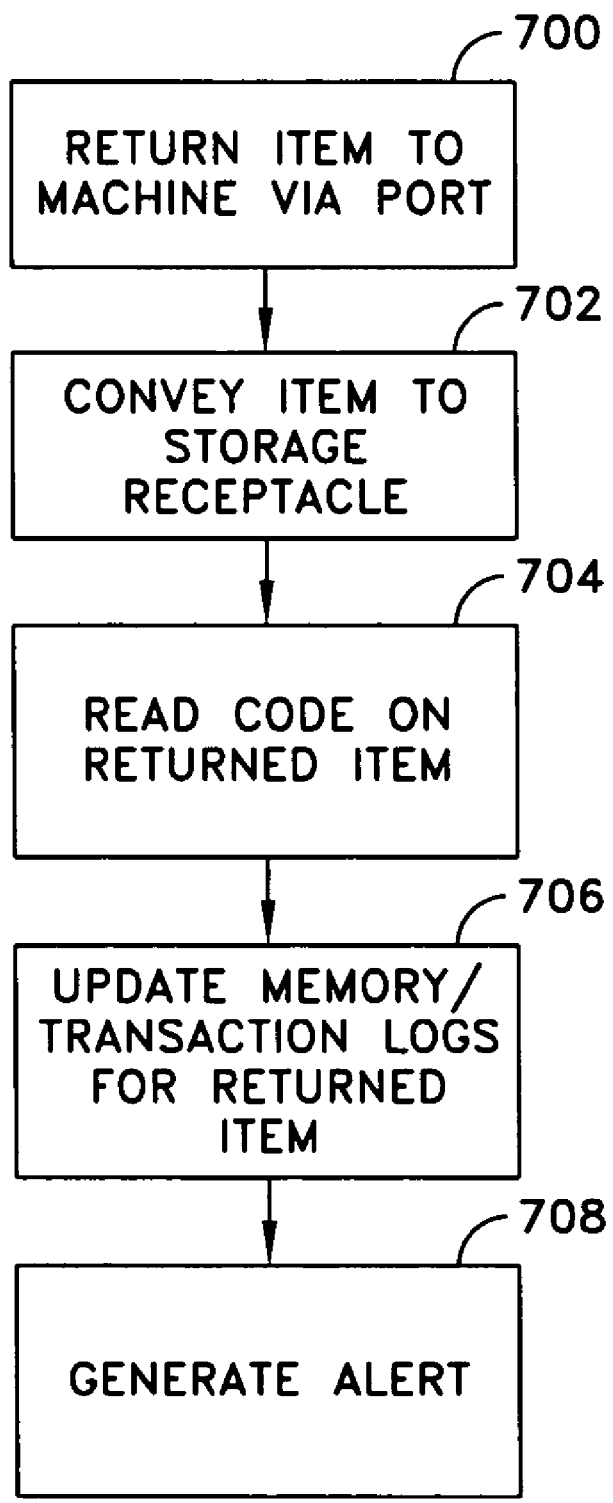
FIG. 7 is an exemplary process flow for implementing quarantine aspects of the present invention.

Referring now to FIG. 7 in conjunction with FIG. 6a-6b, in a system employing RFID functionality, a previously vended unit 22 that incorrectly delivered or mis-vended so as to be undistributable is inserted back into the machine via port 510 (block 700) for storage in quarantine receptacle 810 (block 702). The reader reads (block 704) the code on the returned unit of use item and identifies the item that has been returned to the quarantine area. The system central processing unit compares that item to its transaction log and updates the memory location(s) (block 706) to indicate that the sensed item has been returned to the machine. In an exemplary embodiment, a system transaction log is updated so as to be marked as "returned and quarantined". Once the transaction has been identified as having been incorrectly delivered (i.e. mis-vended) from the inventory cabinet, the transaction is entered into the system. An alert (block 708) may be generated by the CPU so as to alert a remote pharmacy 33 (see FIG. 1) or a central order processing facility of the occurrence of a mis-vend.

As previously discussed, access to the system may be made via a personal identifier card with barcode or magnetic strip identifier. In another embodiment, access is through a biometric identifier such as a fingerprint reader, iris scanner, face recognition software or voice identification software, for example.

In the embodiment in which a paper form is created, or when patient information sheets are used, the office staff who completes the task then enters the information of the transaction into the information system provided for tracking all of the transaction. The system then removes the transaction from the list of pending transactions and places it instead in a "hold and retrieve" queue. When RFID is used, the reader causes the system to automatically recognize the returned item and provides for the CPU to automatically remove the transaction from the "pending" queue to the "hold and retrieve" queue.

In one embodiment, an alert is also sent to the central order processing system so that the central office is made aware that there is an item that has been placed in the "hold and retrieve" queue and therefore, there is a package unit in the quarantine area of the cabinet.

When a new re-stocking order is generated for that specific cabinet, a report may be attached to the reorder listing the specific items that currently exist inside the quarantine receptacle within the cabinet. It is then the responsibility of the employee or representative who restocks the unit to retrieve each item listed on the report and return them to the central warehouse. This allows for absolute controlled tracking of each of these transactions.

Hence, the present invention enables items that are delivered from a controlled access inventory unit but cannot be properly delivered and/or utilized by an authorized recipient, to be quarantined in a secure manner, while providing monitoring of the transaction, recording and logging of events and providing for a clear chain of custody to establish ownership of that item.

Although the system and method of the present invention have been described with respect to pharmaceuticals, various regulated substances may be dispensed including industrial tools such as expensive work tools, hazardous materials, or other substances that require control or regulation. For example, a method and system can be utilized in a factory setting where expensive tools, bits or dies are controlled in their delivery to the factory floor. Remote order entry can be coordinated with delivery of the appropriate item from inventory to the controlled access point for pickup within the factory, thereby streamlining the process and reducing the time necessary for an individual on the shop floor to leave his/her site and get the appropriate tool or item from central inventory storage.

Through embodiments of the present invention, the method and system as described herein enable better monitoring and control of dispensable items such as controlled or scheduled substances. Based on the use of electronic tags or personal identification mechanisms associated with the dispensing of regulated substances, statistics regarding how and when substances are prescribed and dispensed may be collected. These statistics can be used in determining insurance rates, identifying potential problems and for geographic and demographic studies, for example.

It will be understood that the embodiments of the present invention system illustrated and described herein are merely exemplary and that a person skilled in the art can make many variations to the system. All variations of these components are intended to be included within the scope of the invention.

What is claimed is:

1. A system for controlling access to and segregating pharmaceuticals, said system comprising:
   a vending machine containing prepackaged pharmaceuticals to be vended;
   a data input terminal for selecting one of said prepackaged pharmaceuticals, wherein each of said prepackaged pharmaceuticals has a corresponding vending code that is received by said vending machine in order to vend;
   a data key containing a vending code for a specific prepackaged pharmaceutical contained within said vending machine;
   an electronic reader that reads said data key and causes said vending machine to activate and vend said specific prepackaged pharmaceutical;
   a port on said vending machine adapted to receive one of said prepackaged pharmaceuticals previously vended from said vending machine for return; and a repository operably connected to said port for quarantining said returned prepackaged pharmaceuticals, whereby said returned prepackaged pharmaceuticals are separated from the prepackaged pharmaceuticals to be vended.

2. The system according to claim 1, further including a conduit having a first end coupled to said port and a second end coupled to said repository for conveying said returned pharmaceuticals inserted into said port to said repository.

3. The system according to claim 2, wherein the conduit comprises a tube.

4. The system according to claim 1, further including a reader located in the interior of said vending machine and adapted to read indicia on said returned prepackaged pharmaceuticals for identifying said returned prepackaged pharmaceuticals.

5. The system according to claim 4, wherein
said reader comprises an RFID reader; and
said indicia comprises an RFID tag readable by said reader.

6. The system according to claim 4, wherein said reader is located proximal to the receptacle.

7. The system according to claim 4, wherein a processor responsive to said reader updates a memory indicating the identified prepackaged pharmaceutical has been returned.

8. The system according to claim 4, wherein a processor responsive to said reader generates an alert signal indicating that a prepackaged pharmaceutical has been returned.

9. The system according to claim 1, further comprising a slot on an exterior of said vending machine that receives an item having information associated with said returned prepackaged pharmaceutical, and a receptacle located on the interior of said vending machine in communication with said slot that stores said item inserted into said slot, wherein each information item is matched with said corresponding returned prepackaged pharmaceutical for tracking.

10. The system of claim 9, wherein said received item containing information comprises a sheet of paper containing transaction information associated with said returned prepackaged pharmaceutical.

11. A system for controlling access to and segregating dispensable items, said system comprising:
a vending machine containing said dispensable items to be vended;
access control means responsive to selection of one of said dispensable items for causing said vending machine to activate and vend said selected item;
a memory containing transaction information associated with each of the vended items;
a port on said vending machine adapted to receive items previously vended from said vending machine for return;
a repository operably connected to said port for quarantining each of said returned items received by said port, whereby each of said returned items are separated from the items to be vended; and
a processor operative to update said memory to indicate said returned item has been returned to said machine.

12. The system according to claim 11, wherein said dispensable item comprises a prepackaged pharmaceutical.

13. The system according to claim 11, wherein said dispensable item comprises an industrial tool.

14. The system according to claim 11, further comprising a sensor for sensing said returned items.

15. The system according to claim 14, wherein the sensor includes an RFID sensor adapted to read indicia on said returned item for uniquely identifying said returned item.

16. The system according to claim 11, further comprising a conduit for conveying said item inserted into said port to said repository.

17. The system according to claim 11, wherein at least a portion of the access control means is located remotely from the vending machine.

18. A vending machine comprising:
a controller;
a housing comprising:
bins containing dispensable items;
a first opening formed on said housing;
a conveying system responsive to said controller for conveying items to said first opening for vending;
a processor causing updates to inventory records of said items selected for vending;
a second opening on said housing for receiving items previously vended from said machine and inserted into said opening, defining a misvended item;
a conduit for conveying said misvended items inserted into said opening to a receptacle, wherein said second opening is only in communication with said receptacle; and
a sensor sensing said misvended item and generating a signal to cause said processor to update said inventory records indicating said misvended item.

* * * * *